US009829692B2

(12) United States Patent
Reimer et al.

(10) Patent No.: US 9,829,692 B2
(45) Date of Patent: Nov. 28, 2017

(54) OPTICAL OBSERVATION UNIT AND METHOD FOR ENSURING AN UNCHANGING ILLUMINATION INTENSITY WHEN CHANGING THE COLOR TEMPERATURE OF THE ILLUMINATION

(75) Inventors: Peter Reimer, Ellwangen (DE);
Thomas Kratzer, Konigsbronn (DE);
Stefan Ernsperger, Ellwangen (DE);
Bruno Stich, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 845 days.

(21) Appl. No.: 12/760,184

(22) Filed: Apr. 14, 2010

(65) Prior Publication Data
US 2010/0261966 A1 Oct. 14, 2010

(30) Foreign Application Priority Data

Apr. 14, 2009 (DE) .................. 10 2009 017 710

(51) Int. Cl.
*A61B 1/06* (2006.01)
*G02B 21/08* (2006.01)
(Continued)

(52) U.S. Cl.
CPC .......... *G02B 21/082* (2013.01); *A61B 1/0646* (2013.01); *A61B 1/0661* (2013.01);
(Continued)

(58) Field of Classification Search
CPC ... A61B 1/0638; A61B 1/0646; A61B 1/0669; A61B 1/00186; A61B 1/0653;
(Continued)

(56) References Cited

U.S. PATENT DOCUMENTS 3,782,823 A * 1/1974 Kantorski et al. ............ 356/318
4,687,304 A 8/1987 Piller et al.
(Continued)

FOREIGN PATENT DOCUMENTS

DE 35 26 993 2/1986
DE 34 42 218 5/1986
(Continued)

*Primary Examiner* — Alexandra Newton
(74) *Attorney, Agent, or Firm* — Nixon Peabody LLP; Jeffrey L. Costella

(57) ABSTRACT

An optical observation unit (1) has an illumination apparatus (43) for illuminating an observation object (3). The illumination apparatus (43, 143) has a light source (45) emitting illumination light with a first color temperature, and a spectral filter (49) that can be inserted in the illumination beam path. The spectral filter (49) converts the illumination light with the first color temperature into illumination light with a second color temperature. The illumination apparatus further has an attenuator (51) that can be inserted in the illumination beam path in place of the spectral filter (49) and has a transmission characteristic that leads to an intensity reduction of the illumination light with the first color temperature that corresponds to the intensity reduction of the illumination light with the second color temperature by way of the spectral filter (49).

16 Claims, 3 Drawing Sheets

(51) Int. Cl.

| | |
|---|---|
| *A61B 3/00* | (2006.01) |
| *A61B 3/13* | (2006.01) |
| *G02B 26/00* | (2006.01) |
| *G02B 26/02* | (2006.01) |
| *A61B 90/30* | (2016.01) |
| *A61B 90/20* | (2016.01) |
| *G02B 5/20* | (2006.01) |
| *G02B 5/28* | (2006.01) |

(52) U.S. Cl.
CPC .............. *A61B 3/0008* (2013.01); *A61B 3/13* (2013.01); *A61B 90/20* (2016.02); *A61B 90/30* (2016.02); *G02B 26/008* (2013.01); *G02B 26/023* (2013.01); *G02B 5/205* (2013.01); *G02B 5/28* (2013.01)

(58) Field of Classification Search
CPC .. H04N 5/2254; H04N 5/2256; H04N 5/2354; G01J 3/10; G01J 2003/1217; G01J 2003/1221; G01J 3/0213; G01J 3/0248; G01N 21/255; G02B 5/205; G02B 26/02; G02B 21/365; G02B 26/007; G02B 26/023
USPC .................. 359/388; 351/213, 221, 233–236
See application file for complete search history.

(56) References Cited

U.S. PATENT DOCUMENTS

| | | | |
|---|---|---|---|
| 5,022,744 | A | 6/1991 | Leiter |
| 5,703,714 | A | 12/1997 | Kojima |
| 6,226,460 | B1* | 5/2001 | Hino et al. ............... 396/73 |
| 7,224,522 | B2 | 5/2007 | Kawanabe et al. |
| 7,443,579 | B2* | 10/2008 | Kitajima ................. 359/388 |
| 2002/0053639 | A1 | 5/2002 | Katsumata et al. |
| 2002/0097486 | A1 | 7/2002 | Yamaguchi et al. |
| 2004/0080817 | A1 | 4/2004 | Yamaguchi |
| 2006/0056023 | A1* | 3/2006 | Malfait et al. .............. 359/472 |
| 2007/0297175 | A1* | 12/2007 | Glent-Madsen ....... G02B 26/04 362/282 |
| 2008/0068708 | A1 | 3/2008 | Shirota |
| 2008/0123052 | A1* | 5/2008 | Su et al. ................. 351/221 |

FOREIGN PATENT DOCUMENTS

| | | |
|---|---|---|
| DE | 195 13 350 | 10/1995 |
| DE | 10 2007 026 044 | 8/2008 |
| EP | 1 512 998 | 3/2005 |
| EP | 2 015 124 | 1/2009 |

* cited by examiner

OPTICAL OBSERVATION UNIT AND METHOD FOR ENSURING AN UNCHANGING ILLUMINATION INTENSITY WHEN CHANGING THE COLOR TEMPERATURE OF THE ILLUMINATION

BACKGROUND OF THE INVENTION

Field of the Invention

The present invention relates to an optical observation unit, in particular a medico-optical observation unit having an illumination apparatus for illuminating an observation object. The medico-optical observation unit can in particular be a surgical microscope or an endoscope. The invention additionally relates to a method for ensuring an unchanging illumination intensity when changing the illumination from a first color temperature to a second color temperature by inserting or removing a spectral filter in or from the illumination beam path of an optical observation unit.

Description of the Related Art

U.S. Pat. No. 7,443,579 B2 and DE 10 2007 026 044 B3 disclose illumination apparatuses for surgical microscopes which have either a xenon gas discharge lamp or a halogen incandescent lamp as a white-light source. Xenon gas discharge lamps and halogen incandescent lamps both emit what is referred to as white light, but they differ in terms of the color temperature of said light emitted by them. While xenon gas discharge lamps emit light with a correlated color temperature of about 6000° K (often also referred to as "cold white light"), halogen incandescent lamps emit light with a correlated color temperature of about 3000° K (often also referred to as "warm white light").

When conducting ophthalmic surgeries such as cataract surgeries where the lens of the eye is removed, it may be advantageous, depending on the type of defect, to illuminate the operating site in the eye with a correlated color temperature of 3000° K or 6000° K. In cases of cataracts, by way of example, it is typically advantageous to illuminate with a correlated color temperature of 3000° K, since what is referred to as a red reflex, which illuminates the lens, can thus be produced. Said red reflex is brought about by a reddish to orange reflection of the illumination light at the retina. It is therefore advantageous if the light has a high proportion of red, which is the case for a low correlated color temperature. However, if the intention is to render for example opacities in the cornea, in the vitreous body or in the lens or scars in the cornea visible, it is advantageous to use light with a color temperature of about 6000° K, which has higher blue proportions (which undergo more pronounced scattering than the red proportion) than the light with a correlated color temperature of 3000° K. In a cataract operation, the scattering would have a negative effect however, which is why light with a correlated color temperature of about 6000° K is not usually used in such operations.

The surgical microscopes described in U.S. Pat. No. 7,443,579 B2 and DE 10 2007 026 044 B3 have spectral filters in their illumination apparatuses for changing the color temperature of the light emitted by the white-light source, which spectral filters can be inserted in the illumination beam path in order to convert for example the light of a xenon gas discharge lamp with a correlated color temperature of about 6000° K to light with a correlated color temperature of 3000° K, which corresponds to the light of a halogen incandescent lamp. If the red reflex is intended to be used, the spectral filter is inserted in the illumination beam path in order to convert the light from the xenon gas discharge lamp. Patent specification U.S. Pat. No. 7,443,579 B2 moreover describes the use of a halogen incandescent lamp together with a filter, wherein the filter then converts the light with a correlated color temperature of about 3000° K emitted by the halogen incandescent lamp into light with a correlated color temperature of about 6000° K.

Converting light of a first color temperature into light of a second color temperature, however, always entails a loss in intensity due to the wavelength components which are filtered out of the initial emission for conversion purposes. For example, if the intention is to use a xenon gas discharge lamp for illumination with a correlated color temperature of 3000° K, filtering out the corresponding spectral components reduces the illuminance, which can in principle be compensated for by corresponding readjustment of the lamp output. Such an adjustment, however, requires a correspondingly complex electronic arrangement and is not entirely without problems in respect of safety aspects either. If, for example, a transition is made during an eye exam or eye operation from an illumination with a correlated color temperature of 6000° K to an illumination with a correlated color temperature of 3000° K by way of insertion of a filter, and the lamp output is adjusted up in order to compensate for the loss in illuminance, it is necessary for the sake of patient health to ensure that the output of the xenon gas discharge lamp is reduced again as soon as the filter is taken out of the beam path again. This, too, necessitates a correspondingly complex electronic arrangement.

It is therefore an object of the present invention to provide an optical observation unit which enables a switching between illumination light with a first color temperature to illumination light with a second color temperature and in the process solves the abovementioned difficulties by simple means.

It is a further object of the invention to provide an advantageous method for ensuring an unchanging illuminance when changing the color temperature of the illumination by inserting or removing a spectral filter in or from the illumination beam path of an optical observation unit.

SUMMARY OF THE INVENTION

An optical observation unit according to the invention, which can be configured, in particular, as a medico-optical observation unit such as an endoscope or in particular a surgical microscope, comprises an illumination apparatus for illuminating an observation object along an illumination beam path. The illumination apparatus is equipped with a light source, for example a gas discharge lamp, an incandescent lamp, a light-emitting diode (LED) or an organic light-emitting diode (OLED), which emits illumination light with a first color temperature. The illumination apparatus furthermore comprises a spectral filter apparatus which can be inserted in the illumination beam path, wherein the spectral filter apparatus has such a filter characteristic that the illumination light with the first color temperature is converted into illumination light with a second color temperature which differs from the first color temperature. The illumination apparatus further contains an attenuator apparatus which can be inserted in the illumination beam path in place of the spectral filter apparatus and has a transmission characteristic which leads to an intensity reduction of the illumination light, wherein the intensity reduction by way of the attenuator apparatus corresponds to the intensity reduction by way of the spectral filter apparatus. The attenuator apparatus can, in particular, here also itself comprise a spectral filter, for example a yellow filter for filtering out blue proportions in the illumination light. If the attenuator apparatus comprises a spectral filter, it is possible in the spectral filter apparatus inserted in the illumination beam path and in the attenuator apparatus inserted in the illumination beam path for different changes in the color temperature of the light emitted by the light source to result, with the intensity of the illuminations with the different color temperatures being the same in each case. At a given lamp output, inserting the attenuator apparatus in the illumination beam path consequently results in the light from the light source being attenuated with or without a change in its color temperature to the same extent as it would be attenuated in the case of a change in the color temperature using the spectral filter apparatus. If illumination is carried out with the first color temperature and the inserted attenuator apparatus, and then illumination is carried out with the second color temperature, that is to say with the spectral filter apparatus being inserted in the illumination beam path, wherein the attenuator apparatus is replaced by the spectral filter apparatus, the illumination intensity does not change due to the change in color temperature. The illumination intensity likewise remains constant when reverting back from the spectral filter apparatus to the attenuator apparatus. Complicated readjustment of the lamp output is therefore not necessary.

It is also possible within the framework of the invention that the optical observation unit has more than one attenuator apparatus, wherein the attenuator apparatuses each comprise different combinations of attenuator elements and spectral filters which are coordinated with each other such that a plurality of color temperatures with in each case identical illumination intensity can be realized.

The attenuator apparatus can in principle comprise all types of optical elements, as the attenuator element, which reduce the intensity of light without changing the spectrum of the light. Examples of possible attenuator elements are neutral density filters, dielectric neutral filters or apertures. Suitable apertures in this case are in particular single-pinhole apertures, multiple-pinhole apertures or slot apertures. Such apertures are known, for example, from DE 35 26 993 A1 or DE 195 13 350 A1. Compared with neutral density filters, apertures can typically be produced with a better thermal behavior. It is additionally possible to produce them from simple materials using simple processes, for example by etching methods, eroding methods or methods based on laser machining. In addition, apertures are less sensitive than neutral filters. The attenuator element can also comprise a combination of at least one aperture and at least one neutral filter.

The spectral filter apparatus and/or the attenuator apparatus can in principle comprise color filters and/or interference filters as the spectral filters. Due to the lower intensity losses during the filtering of the light, interference filters are, however, advantageous as compared to color filters. If color filters are used, the wavelength proportions which are to be removed from the light are absorbed, leading to a temperature load on the filter and even possible damage to it, in extreme cases resulting in loss of filter effect. If interference filters are used, the wavelength proportions which are to be removed from the light are not absorbed but reflected, as a result of which the temperature load is much lower as compared to color filters.

In one embodiment of the optical observation unit according to the invention, the illumination apparatus comprises a moveable carrier element with a section having the spectral filter apparatus and a section having the attenuator apparatus. The carrier element is arranged such that the section having the spectral filter apparatus or alternatively the section having the attenuator apparatus can be inserted in the illumination beam path. In this case, the carrier element can advantageously be moveably arranged in particular such that it can be moved either into a first position or a second position, that is to say that it only has two positions, wherein the section having the spectral filter apparatus is inserted in the illumination beam path in the first position and the section having the attenuator apparatus is inserted in the illumination beam path in the second position. The result of the fact that only either the first position with the spectral filter apparatus being inserted in the illumination beam path or the second position with the attenuator apparatus being inserted in the illumination beam path can be assumed is that if the spectral filter apparatus is taken out of the illumination beam path, the attenuator apparatus is simultaneously inserted in the illumination beam path and vice versa. A sudden increase or decrease of the illumination intensity, which could be uncomfortable for the patient or, in the worst case, even be harmful, is thus avoided during switchover between illumination light having different color temperatures.

In a first concrete embodiment, the carrier element is a rotatable disk, in particular a circular disk, although it is also possible in principle to use disks in the shape of a partial circle, such as a semicircle. In addition to the circular disks it is also possible, however, to use other geometric disk shapes, for example in the shape of regular or irregular polygons. The rotatable disk comprises a disk section having the spectral filter apparatus and a disk section having the attenuator apparatus, wherein the disk section having the spectral filter apparatus or, alternatively, the disk section having the attenuator apparatus can be inserted in the illumination beam path by rotating the disk. If, for example, a circular disk, i.e. a completely round disk, is used in this embodiment, the change between spectral filter apparatus and attenuator apparatus can be effected by rotating in always the same rotational direction without running the risk that neither the attenuator apparatus nor the spectral filter apparatus is arranged in the illumination beam path. If the disk is merely in the shape of a partial circle, for example a semicircular disk, it is still possible to effect the change by rotation in always the same rotational direction, but care must be taken in that case that the rotation is carried out far enough for either the spectral filter apparatus or the attenuator apparatus to always be arranged in the beam path. In other words, it is necessary to avoid a mere half-rotation, in which case the missing part of the disk would be arranged in the beam path, meaning that neither the spectral filter apparatus nor the attenuator apparatus would be arranged in the beam path. This problem can be avoided, however, during use of a partial circular disk, if the partial circular disk can be pivoted between two end positions in both rotational directions. Such a pivoting embodiment is of course also possible if the circular disk is in the form of a complete circle.

In a second concrete embodiment, the carrier element can be moved between a first end position and a second end position along a linear path. The section having the spectral filter apparatus is inserted in the illumination beam path in the first end position, and the section having the attenuator apparatus is inserted in the illumination beam path in the second end position. It is also possible in this embodiment to prevent the situation where neither the attenuator apparatus nor the spectral filter apparatus is inserted in the illumination beam path.

The carrier can be configured in particular as an etched part, eroded part or a part produced by laser machining, which makes it possible for the part containing the attenuator element to be etched directly into the carrier. In this manner, a cost-effective aperture solution, in particular a solution involving a multiple-pinhole aperture, can be realized.

In the optical observation unit according to the invention, the light source which emits the illumination light with a first color temperature can be, in particular, a gas discharge lamp, such as a xenon lamp, or an incandescent lamp, such as a halogen incandescent lamp. If the light source used is a gas discharge lamp, the spectral filter apparatus converts the illumination light into illumination light with the color temperature of an incandescent lamp. If the light source used is an incandescent lamp, however, it converts the illumination light into illumination light with the color temperature of a gas discharge lamp. The color temperatures which are frequently required especially in ophthalmology can be realized in a simple manner using this embodiment. However, spectral filter apparatuses for producing color temperatures other than those of gas discharge lamps or halogen incandescent lamps can of course also be used.

The invention further provides a method for ensuring an unchanging illumination intensity of an optical observation unit with an illumination apparatus having a light source when changing from an illumination with a first color temperature to an illumination with a second color temperature or vice versa by inserting or removing a spectral filter apparatus comprising a spectral filter in or from the illumination beam path. If the illumination with the first color temperature is changed to an illumination with the second color temperature, an attenuator apparatus located in the illumination beam path and having an alternator element is exchanged for the spectral filter apparatus. However, if an illumination with the second color temperature is changed to an illumination with the first color temperature, the spectral filter apparatus is exchanged for the attenuator apparatus.

The advantages that can be achieved with the method according to the invention result from the above description of the optical observation unit according to the invention, which is configured for carrying out the method according to the invention.

BRIEF DESCRIPTION OF THE DRAWINGS

Further features, characteristics and advantages of the invention result from the following description of exemplary embodiments with reference to the appended figures.

DETAILED DESCRIPTION OF THE PREFERRED EMBODIMENTS

Figure 1:
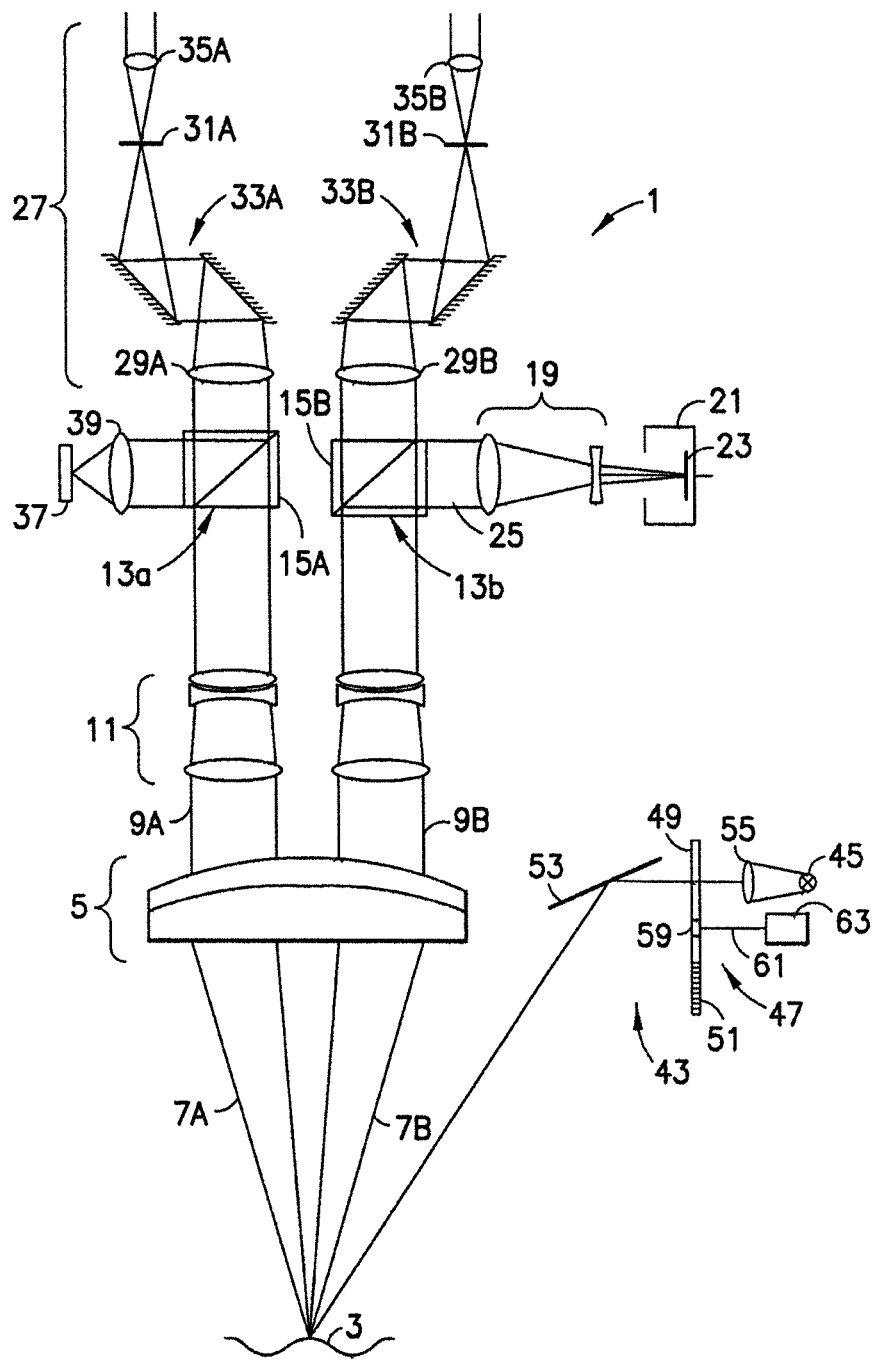
FIG. 1 shows a first exemplary embodiment for the optical observation unit according to the invention.

With reference to FIG. 1, the principle construction of an optical observation unit according to the invention will be illustrated below using the example of a surgical microscope.

The surgical microscope 1 shown in FIG. 1 comprises, as essential components, an objective 5 which is to face an observation object 3 and is illustrated in the present exemplary embodiment as an achromatic or apochromatic lens constructed from at least two partial lenses which are cemented together. The observation object 3 is arranged in the focal plane of the objective 5, with the result that the tissue region 3 is imaged to infinity, that is to say a diverging beam bundle 7 emanating from the tissue region 3 is converted into a parallel beam bundle 9 as it passes through the objective 5.

Instead of merely using an achromatic lens, as is used as objective 5 in the present exemplary embodiment, it is also possible to use an objective lens system comprising a plurality of individual lenses, such as what is referred to as a vario objective, which can be used to vary the working distance of the surgical microscope 1, i.e. the distance from the focal plane to the objective 5. In such a vario system, the tissue region 3 arranged in the focal plane is also imaged to infinity, with the result that in a vario objective, a parallel beam bundle is also present on the observer side.

A magnification changer 11, which can be configured either as a zoom system for changing the magnification factor in an infinitely variable manner, as in the exemplary embodiment illustrated, or as what is referred to as a Galilean changer for changing the magnification factor in a infinitely variable manner on the observer side of the objective 5. In a zoom system constructed, for example, from a lens combination using three lenses, the two object-side lenses can be displaced in order to vary the magnification factor. However, the zoom system can also in fact have more than three lenses, such as four or more lenses, with the outermost lenses being able to be arranged fixedly in that case. In contrast, a Galilean changer has a plurality of fixed lens combinations which represent various magnification factors and can be inserted in the beam path in an alternating manner. Both a zoom system and a Galilean changer convert an object-side parallel beam bundle into an observer-side parallel beam bundle having a different bundle diameter. The magnification changer 11 is in this case already part of the binocular beam path of the surgical microscope 1, that is to say it has a specific lens combination for each stereoscopic partial beam path 9A, 9B of the surgical microscope 1.

On the observer side, the magnification changer 11 is adjoined by an interface arrangement 13A, 13B, which can be used to connect external equipment to the surgical microscope 1 and which in the present exemplary embodiment comprises beam-splitter prisms 15A, 15B. However, in principle, other types of beam splitters can also be used, for example partly transparent mirrors. In the present exemplary embodiment, the interfaces 13A, 13B are used for coupling a beam bundle out of the surgical microscope 1 (beam-splitter prism 15B) and for coupling a beam bundle into one of the partial beam paths of the surgical microscope 1 (beam-splitter prism 15A).

In the present exemplary embodiment, the beam-splitter prism 15A in the partial beam path 9A serves for mirroring information or data for a user into the partial beam path 9A of the surgical microscope 1 with the aid of a display 37, for example a digital mirror device (DMD) or an LCD display, and an associated optical system 39, via the beam-splitter prism 15A. A camera adaptor 19 with a camera 21 attached thereto is arranged on the interface 13B in the other partial beam path 9B, which camera is equipped with an electronic image sensor 23, for example a CCD sensor or a CMOS sensor. An electronic and, in particular, a digital image of the tissue region 3 can be recorded by means of the camera 21.

A binocular tube 27 adjoins the interface 13 on the observer side. This tube has two tube objectives 29A, 29B, which focus the respective parallel beam bundle 9A, 9B onto an intermediate image plane 31, that is to say, which image the observation object 3 on the respective intermediate image plane 31A, 31B. The intermediate images located in the intermediate image planes 31A, 31B are finally imaged to infinity again by eyepiece lenses 35A, 35B and so an observer, for example a treating medical practitioner or his assistant, can observe the intermediate image with a relaxed eye. Moreover, there is an increase in the distance between the two partial beam bundles 9A, 9B within the binocular tube by means of a mirror system or by means of prisms 33A, 33B in order to match said distance to the eye separation of the observer. The mirror system or the prisms 33A, 33B is additionally used to right the image.

Moreover, the surgical microscope 1 is equipped with an illumination apparatus 43, which can be used to illuminate the tissue region 3 with broadband illumination light. For this, the illumination apparatus 43 has a white-light source, for example a halogen incandescent lamp or a gas discharge lamp. In the present exemplary embodiment, the white-light source 45 is formed by a xenon lamp, which emits what is referred to as cold white light with a correlated color temperature of about 6000° K. The light emanating from the xenon lamp 45 is directed, via a deflection mirror 53, in the direction of the surface of the tissue region 3 in order to illuminate the latter. Additionally, an illumination optical system 55 is present in the illumination apparatus 43 and ensures uniform illumination of the entire tissue region 3.

It should be pointed out that the illumination beam path illustrated in FIG. 1 is highly schematic and does not necessarily give the actual illumination beam path. The illumination beam path can in principle be in the form of what is referred to as oblique illumination, which is closest to the schematic illustration in FIG. 1. In the case of such an oblique illumination, the beam path extends at a relatively large angle (6° or more) with respect to the optical axis of the objective 5 and can, as shown in FIG. 1, extend entirely outside the objective. However, there is the alternative of allowing the illumination beam path of the oblique illumination to extend through a marginal region of the objective 5. A further option for arranging the illumination beam path is what is referred to as 0° illumination, in the case of which the illumination beam path extends through the objective 5 and is coupled into the objective between the two partial beam paths 9A, 9B along the optical axis of the objective 5 in the direction of the tissue region 3. Finally, it is also possible for the illumination beam path to be designed as what is referred to as coaxial illumination, in which there is a first and a second partial illumination beam path. The partial beam paths are coupled into the surgical microscope 1 parallel to the optical axes of the partial observation beam paths 9A, 9B via one or more beam splitters, with the result that the illumination runs coaxially with the two partial observation beam paths.

The illumination apparatus 43 with the white-light source 45 does not have to be arranged directly at the surgical microscope 1, as is shown in FIG. 1. Instead it may be arranged at a distance from the surgical microscope 1, for example at the microscope stand. In that case, an optical waveguide is used to guide the light from the light source apparatus to the surgical microscope 1.

The illumination apparatus 43 additionally comprises a filter wheel 47 with a spectral filter 49 that filters a blue spectral proportion out of the illumination light from the xenon lamp 45 in order to convert the correlated color temperature of the light from the xenon lamp of about 6000° K into a correlated color temperature of about 3000° K, which approximately corresponds to the light of a halogen lamp. In this case, the spectral filter 49 can in principle be designed as a color filter or an interference filter. The spectral filter 49 forms in the present exemplary embodiment, in conjunction with the part of the filter wheel that contains the filter 49, the spectral filter apparatus.

In addition to the spectral filter 49, the filter wheel 47 moreover has an attenuator 51 that allows the entire spectrum of the light emitted by the xenon lamp 45 to pass, i.e. without a wavelength component of the spectrum being filtered out, but which attenuates a percentage of the light intensity uniformly over all the wavelengths of the spectrum of the xenon lamp 45. The attenuator 51 in the present exemplary embodiment forms in conjunction with that part of the filter wheel 47 that contains the attenuator 51 the attenuator apparatus. Transmission of the attenuator 51 is in this case coordinated with the illuminance loss when changing the color temperature by way of the spectral filter 49 such that the observation object 3 is illuminated when the attenuator 51 is inserted in the illumination beam path with the same illuminance as when the spectral filter 49 is inserted in the illumination beam path. As a result, the illuminance does not change at the site of the observation object 3 when the attenuator 51 is changed to the spectral filter 49 in the illumination beam path. Readjustment of the lamp output is thus not necessary if a transition is made from an illumination with a correlated color temperature of 6000° K to an illumination with a correlated color temperature of 3000° K. In addition, increased stress on the patient can be avoided when changing from the illumination converted in terms of its color temperature to the illumination with the original light of the xenon lamp 45 by changing from the spectral filter 49 to the attenuator 51.

Figure 2:
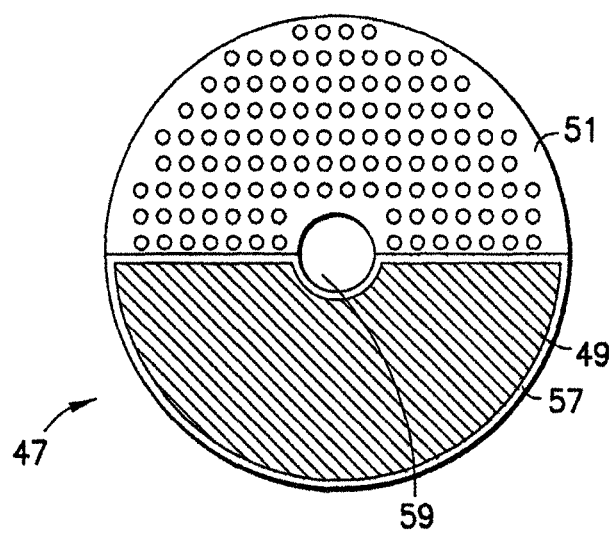
FIG. 2 shows a filter wheel used in the optical observation unit of FIG. 1.

A plan view of the filter wheel 47 in the form of a circular disk is illustrated in FIG. 2. The filter wheel 47 can be, for example, an etched part, eroded part or a laser-machined part made of plastic, ceramic or metal, with the attenuator 51 having a multiplicity of holes etched, eroded or lasered into one half in the form of a multiple-pinhole aperture, as is shown highly schematically in FIG. 2. The transmittance of the attenuator can be set in this case by way of the opening diameter of the holes and/or the separation of the holes. Slots or openings of different shapes can also be used instead of the holes shown.

The other half of the filter wheel 47 is in the form of a carrier for the spectral filter 49. The carrier has an opening into which the spectral filter 49 is placed. The edge 57 of the opening and the spectral filter 49 placed in the opening can be seen in FIG. 2.

A receiver 59 for the drive shaft 61 of a drive 63, such as a rotating motor, or of a manually operated actuator such as a rotating wheel, which is used to move the filter wheel 47 in a defined manner in two different rotational positions, is located at the center of the filter wheel. In one rotational position, which is shown in FIG. 1, the spectral filter 49 is located in the illumination beam path, while in the other rotational position the multiple-pinhole aperture 51 is located in the illumination beam path.

Although the filter wheel illustrated in FIG. 2 has just two sectors, of which one contains the spectral filter 49 and the other the multiple-pinhole aperture 51, the number of sectors may also be higher. For example, it is possible for four or six sectors to be present, wherein the sectors extend in each case across a quarter or a sixth of the circumference of the circle. Attenuators and spectral filters are in this case alternately arranged in the sectors. If such a filter wheel is used, a change between the attenuator 51 and the spectral filter 49 can take place by way of a rotation which is clearly less than if the filter wheel shown in FIG. 2 is used. This is because in each case only a quarter of a rotation or a sixth of a rotation needs to take place for a change, as compared to a half rotation in the filter wheel 47 shown in FIG. 2. The number of sectors in the filter wheel 47 can of course also be higher than six. The number of sectors which can be accommodated on the filter wheel 47 depends in this case only on the width of a sector necessary for it to cover the entire illumination beam path at the location of the filter wheel.

Rather than the multiple-pinhole aperture shown in FIG. 2, the filter wheel 47 can also contain a neutral density filter made of glass or plastic, which is placed in an opening of the carrier, as is also the case with the spectral filter.

A second exemplary embodiment for the surgical microscope according to the invention is described below with reference to FIG. 3. The figure shows only the light source apparatus 143 and the deflection mirror 53. All the elements of the surgical microscope of the second exemplary embodiment which are not shown are identical to those in the first exemplary embodiment and therefore will not be explained again.

Figure 4:
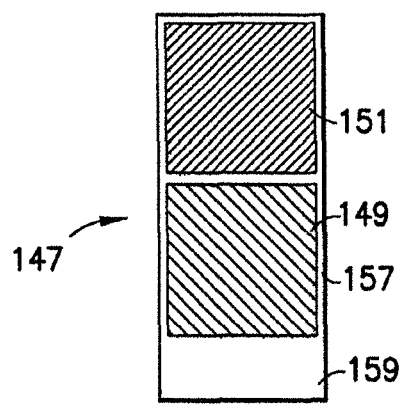
FIG. 4 shows a filter carrier as is used in the second exemplary embodiment.

In the surgical microscope according to the second exemplary embodiment, a filter disk 147 in the form of a slide is used instead of a filter wheel 47, which filter disk can be displaced along a linear path. FIG. 4 shows a plan view of the filter disk 147 of the second exemplary embodiment. The filter disk comprises a carrier which has a mounting section 159 for mounting to a drive, for example to the rotor 161 of a linear motor. The carrier additionally has a frame 157 for the placement of a neutral density filter 151 and of a spectral filter 149. In the present exemplary embodiment, the spectral filter 149 forms in, conjunction with that part of the frame 157 which contains the filter 149, the spectral filter apparatus, and the neutral density filter 151 forms, in conjunction with that part of the frame 157 which contains the neutral density filter 151, the spectral filter apparatus. The transmission of the neutral density filter 151 is here coordinated in terms of the illuminance loss by way of the spectral filter when converting the light into light with a different color temperature such that the observation object 3 experiences the same, or largely the same, illuminance independently of whether the spectral filter 149 or the neutral density filter 151 is inserted in the illumination beam path. It is also possible to use an aperture, as was described with reference to the first exemplary embodiment, rather than the neutral density filter, as an attenuator. It is also possible to use a dielectric neutral filter rather than the neutral density filter.

The rotor 161 mounted to the mounting section 159 can be used to move the filter disk 147 between a first linear end position and a second linear end position. While the neutral density filter 151 is inserted in the illumination beam path in one linear end position, as is shown in FIG. 3, the spectral filter 149 is inserted in the illumination beam path in the other linear end position. The direction of movement of the filter disk 147 is shown in FIG. 3 by way of a double-headed arrow. The filter disk can also be moved manually rather than by the use of a motor, for example by way of an actuator in the form of a slide, lever etc. mounted on the microscope.

A third exemplary embodiment for the surgical microscope according to the invention will be described below with reference to FIG. 5. The third exemplary embodiment is a modification of the second exemplary embodiment. Elements which correspond to elements in the second exemplary embodiment have the same reference numerals as used in FIG. 3 and will not be explained again.

Figure 3:
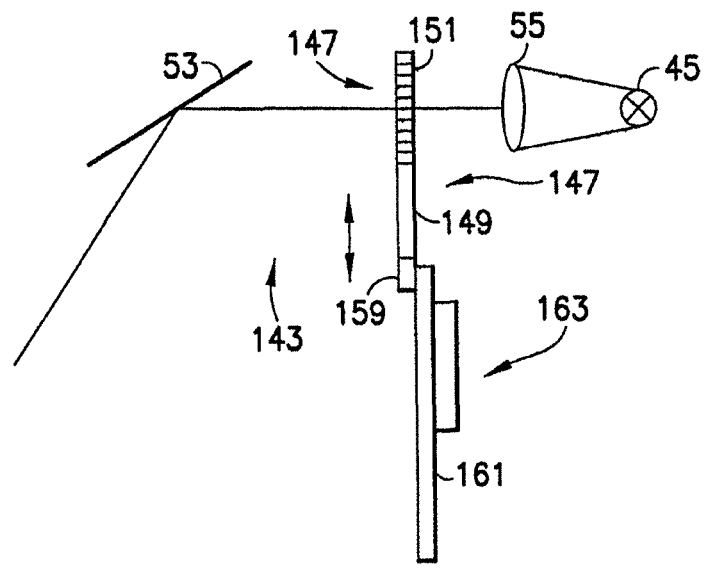
FIG. 3 shows a detail of a second exemplary embodiment for the optical observation unit according to the invention.
Figure 5:
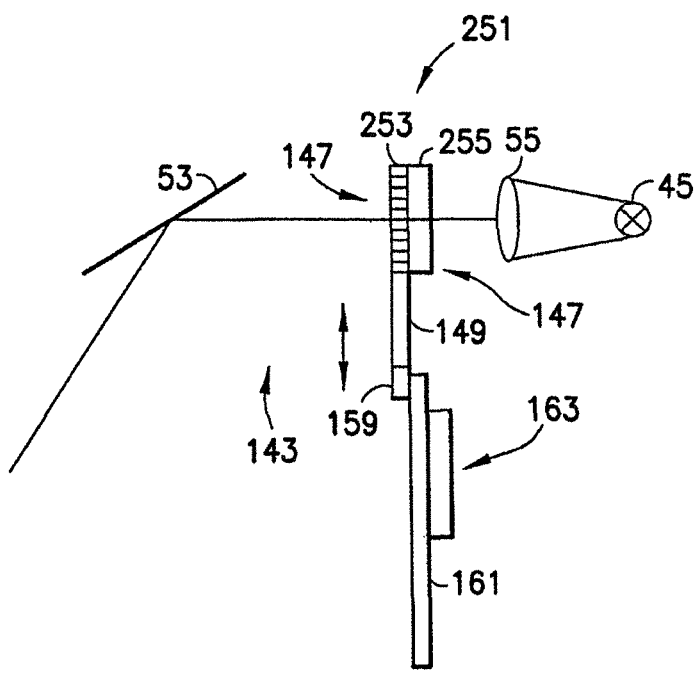
FIG. 5 shows a detail of a third exemplary embodiment for the optical observation unit according to the invention.

The exemplary embodiment shown in FIG. 5 differs from the exemplary embodiment shown in FIG. 3 in that the attenuating apparatus comprises not only an attenuating element 253 but also a spectral filter 255 which changes the color temperature of the light emanating from the light source 45. The spectral filter 255, which may be in the form of a color filter or an interference filter, is mounted in the present exemplary embodiment on the filter disk 147 such that it is connected upstream of the attenuating element 253 in the beam path. However, it may also be mounted on the opposite side of the filter disk 147, with the result that it is connected downstream of the attenuator element 253 in the beam path. The filter characteristic of the spectral filter 255 of the attenuator apparatus differs from the filter characteristic of the spectral filter 149 in the spectral filter apparatus, that is to say the change in color temperature caused by the spectral filter 255 of the attenuator apparatus differs from the change in color temperature brought about by the spectral filter 149 of the spectral filter apparatus.

In the third exemplary embodiment of the invention, the color temperature of the light emanating from the light source 45 is changed both by the spectral filter apparatus and by the attenuator apparatus. If other combinations of an attenuator element and a spectral filter are used, more than two color temperatures can be realized. The respective combinations of attenuator elements and spectral filters are here coordinated with one another such that the object is illuminated with the same intensity at each color temperature.

Although the attenuator apparatus 251 with a combination of an attenuator element 253 and a spectral filter 255 has been described with reference to the filter disk 147 which is moveably arranged, it is also possible for a filter wheel 47, as has been described with reference to FIGS. 1 and 2, to be equipped with such a combination. In a filter wheel of this type it is possible in particular for each filter wheel sector to be equipped with a different combination of attenuator element and spectral filter, such that a number of color temperatures which corresponds to the number of filter wheel segments can be realized. In particular, one of the filter wheel sectors may have only one attenuator, with the result that the illumination radiation transmitted by this sector corresponds in terms of its color temperature to that of the light source.

Although the invention has been explained using three concrete exemplary embodiments, deviations from the exemplary embodiments are also possible. Thus for example, the attenuator and the spectral filter need not be arranged on a common carrier. Rather, both can also be arranged on different carriers which can be inserted alternately in the illumination beam path. The spectral filter or the attenuator also does not need to be inserted in the illumination beam path along a linear path or along a rotational path. It is also possible to insert spectral filter and attenuator alternately in the illumination beam path by way of a pendular movement.

Although xenon lamps are used as white-light sources in the exemplary embodiments, it is also possible in principle to use as white-light sources halogen lamps or electroluminescence emitters, such as light-emitting diodes or organic light-emitting diodes. If a halogen lamp is used, for example, the spectral filter may be configured such that it converts the light from the halogen lamp, which has a correlated color temperature of about 3000° K, into light with a higher correlated color temperature, in particular into light with a correlated color temperature of about 6000° K, by filtering out red spectral proportions.

What is claimed is:

1. An optical observation unit comprising:
an illumination apparatus for illuminating an observation object along an illumination beam path, the illumination apparatus having a light source emitting illumination light at a first constant intensity level with a first color temperature, and a spectral filter apparatus that is selectively insertable into the illumination beam path, with the spectral filter apparatus having a spectral filter with a filter characteristic so that the spectral filter converts the illumination light with the first color temperature into illumination light at the observation object with a second color temperature that is different from the first color temperature and so that an intensity of the light at the observation object is reduced from the first constant intensity level to a second constant intensity level, at least one attenuator apparatus with an attenuator element that can be inserted in the illumination beam path in place of the spectral filter apparatus, the attenuator element having a transmission characteristic that leads to an intensity reduction of the illumination light at the observation object, wherein the optical observation unit is configured to simultaneously insert the attenuator apparatus in the illumination beam path when the spectral filter apparatus is taken out of the illumination beam path, the illumination intensity reduction at the observation object caused by the spectral filter is equal to the illumination intensity reduction at the observation object caused by the attenuator element, so that the illumination intensity at the observation object remains constant, at the second constant intensity level, when one of the spectral filter and the attenuator apparatus is replaced by the other of the spectral filter and the attenuator apparatus, and one of the spectral filter and the attenuator apparatus is replaced by the other of the spectral filter and the attenuator apparatus based on intensity level and color temperature of the light source.

2. The optical observation unit of claim 1, wherein the attenuator apparatus comprises a neutral density filter or a dielectric neutral filter as the attenuator element.

3. The optical observation unit of claim 1, wherein the attenuator apparatus comprises an aperture as the attenuator element.

4. The optical observation unit of claim 1, characterized in that the attenuator apparatus comprises a spectral filter.

5. The optical observation unit of claim 4, characterized in that at least two attenuator apparatuses with different spectral filters are present.

6. The optical observation unit of claim 1, wherein the spectral filter is a color filter.

7. The optical observation unit of claim 1, wherein the spectral filter is an interference filter.

8. The optical observation unit of claim 1, wherein the illumination apparatus comprises a moveable carrier element with a section forming the spectral filter apparatus and a section forming the attenuator apparatus, the carrier element being arranged so that the section forming the spectral filter apparatus and the section forming the attenuator apparatus are insertable alternatively in the illumination beam path.

9. The optical observation unit of claim 8, wherein the carrier element is moveably arranged for movement into either a first position or a second position, the section forming the spectral filter apparatus being inserted in the illumination beam path when the carrier element is in the first position and the section forming the attenuator apparatus being inserted in the illumination beam path when the carrier element is in the second position.

10. The optical observation unit of claim 8, wherein the carrier element is a rotatable disk with a first disk section forming the spectral filter apparatus and a second disk section forming the attenuator apparatus, wherein the disk section forming the spectral filter apparatus or, alternatively, the disk section forming the attenuator apparatus can be inserted in the illumination beam path by rotating the disk.

11. The optical observation unit of claim 8, characterized in that the carrier element can be moved between a first end position and a second end position along a linear path, wherein the section forming the spectral filter apparatus is inserted in the illumination beam path in the first end position, and the section forming the attenuator apparatus is inserted in the illumination beam path in the second end position.

12. The optical observation unit of claim 8, wherein the carrier (47) is an etched part, an eroded part or a part machined by laser.

13. The optical observation unit of claim 1, wherein the light source that emits the illumination light with a first color temperature is a gas discharge lamp or an incandescent lamp, and, if a gas discharge lamp is used, the spectral filter apparatus converts the illumination light from the gas discharge lamp into illumination light with the color temperature of an incandescent lamp and, if an incandescent lamp is used, the spectral filter apparatus converts the illumination light from the incandescent lamp into illumination light with the color temperature of a gas discharge lamp.

14. The optical observation unit of claim 1, wherein the optical observation apparatus is an endoscope or surgical microscope.

15. A method for ensuring an unchanging illumination intensity of an optical observation unit of claim 1, comprising:
illuminating, by the light source of the illumination apparatus, the observation object when changing from the illumination with the first color temperature to an illumination with the second color temperature or vice versa;
inserting or removing a spectral filter apparatus comprising a spectral filter in or from the illumination beam path, wherein if the illumination with the first color temperature is changed to an illumination with the second color temperature, the attenuator apparatus located in the illumination beam path is exchanged for the spectral filter apparatus, or, if the illumination with the second color temperature is changed to an illumination with the first color temperature, the spectral filter apparatus is exchanged for the attenuator apparatus.

16. An optical observation unit comprising:
an illumination apparatus for illuminating an observation object along an illumination beam path, the illumination apparatus having a light source emitting illumination light at a first constant intensity level with a first color temperature, and a spectral filter apparatus that is selectively insertable into the illumination beam path, with the spectral filter apparatus having a spectral filter with a filter characteristic so that the spectral filter converts the illumination light with the first color temperature into illumination light at the observation object with a second color temperature that is different from the first color temperature and so that an intensity of the light at the observation object is reduced from the first constant intensity level to a second constant intensity level, at least one attenuator apparatus with an attenuator element that can be inserted in the illumination beam path in place of the spectral filter apparatus, the attenuator element having a transmission characteristic that leads to an intensity reduction of the illumination light at the observation object, wherein the optical observation unit is configured to simultaneously insert the attenuator apparatus in the illumination beam path when the spectral filter apparatus is taken out of the illumination beam path, the illumination intensity reduction at the observation object caused by the spectral filter is equal to the illumination intensity reduction at the observation object caused by the attenuator element, so that the illumination intensity at the observation object remains constant, at the second constant intensity level, when one of the spectral filter and the attenuator apparatus is replaced by the other of the spectral filter and the attenuator apparatus, the spectral filter apparatus and the attenuator apparatus are part of a wheel such that one half of the wheel comprises the spectral filter apparatus and the other half of the wheel comprises the attenuator apparatus, and one of the spectral filter and the attenuator apparatus is replaced by the other of the spectral filter and the attenuator apparatus based on intensity level and color temperature of the light source.

* * * * *